United States Patent
Kaizik et al.

(12) 
(10) Patent No.: US 6,331,657 B1
(45) Date of Patent: Dec. 18, 2001

(54) PROCESS FOR PREPARING HIGHER OXO ALCOHOLS FROM OLEFIN MIXTURES BY TWO-STAGE HYDROFORMYLATION

(75) Inventors: Alfred Kaizik; Bernhard Scholz; Walter Toetsch, all of Marl; Wilfried Bueschken, Haltern; Franz Nierlich, Marl, all of (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/396,371

(22) Filed: Sep. 15, 1999

(30) Foreign Application Priority Data

Sep. 9, 1998 (DE) .............................. 198 42 368

(51) Int. Cl.⁷ .................. C07C 29/16; C07C 29/141; C07C 29/149

(52) U.S. Cl. .................. 568/882; 568/852; 568/857; 568/881; 568/883; 568/884; 568/885; 568/909; 585/275; 585/276

(58) Field of Search .................. 568/852, 857, 568/881, 882, 883, 884, 885, 909; 585/275, 276

(56) References Cited

U.S. PATENT DOCUMENTS

| | | | |
|---|---|---|---|
| 4,533,755 | 8/1985 | Cornils et al. | 568/454 |
| 5,675,045 | 10/1997 | Bueschken et al. | 568/881 |
| 5,728,891 | 3/1998 | Bueschken et al. | 568/376 |
| 5,756,856 | 5/1998 | Bueschken et al. | 568/462 |
| 5,831,135 | 11/1998 | Bueschken et al. | 568/881 |

FOREIGN PATENT DOCUMENTS

| | | |
|---|---|---|
| 1 935 900 | 2/1971 | (DE) . |
| 32 32 557 A1 | * 9/1983 | (DE) . |
| 0 183 545 | 6/1986 | (EP) . |
| 0 326 674 A2 | * 8/1989 | (EP) . |
| 0 850 905 A1 | * 7/1998 | (EP) . |

OTHER PUBLICATIONS

J. Falbe, "Hydroformylation. Oxo Synthesis, Roelen Reaction", New Synthesis with Carbon Monoxide, Springer–Verlag, Berlin, Heidelberg, New York, 1980, pp. 164–165.*
Kirk Othner, Encyclopedia of Chemical Technology, Vo. 17, 4$^{th}$ Edition, John Wiley & Sons, pp. 902–919 (1995).*
Barry L. Haymore et al, Regioselectivity in Hydroformylation of Linear and Branched Octenes using $Hc_0(CO)_4$, Annals of the New York Acad. Sci, 1983, pp. 159–175.*
J. Falbe, "Effect of Reaction Conditions on Conversion, Selectivity and Operations of the Oxo Synthesis", New Synthesis with Carbon Monoxide, Springer–Verlag, Berlin, Heidelberg, New York, pp. 93–100 (1981).*

* cited by examiner

Primary Examiner—Peter O'Sullivan
(74) Attorney, Agent, or Firm—Oblon, Spivak, McClelland, Maier & Neustadt, P.C.

(57) ABSTRACT

A process for preparing higher oxo alcohols from mixtures of isomeric olefins having from 5 to 24 carbon atoms by two-stage hydroformylation in the presence of a cobalt catalyst or rhodium catalyst at elevated temperature and at elevated pressure, which comprises selectively hydrogenating the first hydroformylation stage reaction mixture, separating the hydrogenation mixture in a distillation into crude alcohol and low-boilers predominantly consisting of olefins, passing these low-boilers to the second hydroformylation stage, again selectively hydrogenating the second hydroformylation stage reaction mixture, separating the hydrogenation mixture in one distillation into crude alcohol and low-boilers, working up the crude alcohol by distillation to pure alcohol and taking off at least some of the low-boilers to discharge saturated hydrocarbons.

22 Claims, 2 Drawing Sheets

PROCESS FOR PREPARING HIGHER OXO ALCOHOLS FROM OLEFIN MIXTURES BY TWO-STAGE HYDROFORMYLATION

BACKGROUND OF THE INVENTION

1. Field of the Invention

The present invention relates to a process for preparing higher oxo alcohols by two-stage hydrofornylation of olefin mixtures, which includes selective hydrogenation of the hydroformylation mixtures.

2. Description of the Background

It is known that higher alcohols, in particular those having from 6 to 25 carbon atoms, can be prepared by catalytic hydroformylation (or oxo reaction) of the olefins having one carbon atom less and subsequent catalytic hydrogenation of the aldehyde- and alcohol-containing reaction mixtures. The alcohols are predominantly used as starting materials for the preparation of plasticizers or detergents.

The type of catalyst system and the optimum reaction conditions for the hydroformylation are dependent on the reactivity of the olefin used. The dependence of the reactivity of olefins on their structure is described, for example, by J. Falbe, New Syntheses with Carbon Monoxide, Springer-Verlag, Berlin, Heidelberg, New York, 1980, pages 95 ff. The varying reactivity, especially of the isomeric octenes, is likewise known (B. L. Haymore, A. van Hasselt, R. Beck, Annals of the New York Acad. Sci., 415 (1983), pages 159–175).

Industrial olefin mixtures which are used as starting materials for the oxo synthesis comprise olefin isomers of the most varied structures having differing degrees of branching, differing position of the double bond and, in some cases, even differing carbon numbers. This applies especially to olefin mixtures which have been produced by dimerization, trimerization or further oligomerization of $C_2$–$C_5$ olefins or other easily accessible higher olefins or by co-oligomerization of the olefins. As examples of typical isomeric olefin mixtures which can be reacted by rhodium-catalyzed, or preferably by cobalt-catalyzed, hydroformylation to give the corresponding aldehyde mixtures and alcohol mixtures, tripropenes and tetrapropenes and dibutenes, tributenes and tetrabutenes may be mentioned.

The rate of the hydroformylation reaction decreases with increasing carbon number and with the degree of branching. The reaction rate of linear olefins can be greater by a factor of 5 to 10 than that of the branched isomers. The position of the double bond in the olefin also influences the reactivity. Olefins having a terminal double bond react markedly more rapidly as compared to isomers having an internal double bond. Because of the differing reactivity of the olefin isomers, relatively long reaction times are required if it is desired to achieve the most substantial possible conversion of the olefins. However, as a result, the product yield is decreased due to unwanted side reactions and secondary reactions. This also occurs if attempts are made to shorten the reaction times by higher reaction temperatures. Especially because of the varying reactivity of the isomers, it is difficult to achieve high conversion rates and simultaneously high selectivities in the hydroformylation of olefin mixtures. This applies in particular to single-stage hydroformylations.

According to DE 32 32 557 A1, alcohols are prepared by a two-stage hydroformylation of monoolefins having from 3 to 20 carbon atoms. In the first reaction stage, the olefins are converted to the aldehyde, using a cobalt catalyst, with degrees of conversion of from 50 to 90%, the formation of alcohols being suppressed. The cobalt catalyst is then removed from the reaction mixture and this reaction mixture is hydroformylated again in a second stage using a cobalt organophosphine complex as catalyst. At the same time, the aldehyde formed in the first stage is hydrogenated to the alcohol. A disadvantage in this process is that, particularly in the second hydroformylation stage, a considerable part of the olefins is hydrogenated instead of being hydroformylated.

Accordingly, there remains a need for improved processes for preparing alcohols via the oxo reaction.

SUMMARY OF THE INVENTION

It is an object of the invention to provide a process for preparing higher oxo alcohols from the corresponding olefin mixtures, which combines high conversion rates with high selectivities, that is also distinguished by high space-time yields.

The object of the invention, and others, may be accomplished with a process for preparing higher oxo alcohols from mixtures of isomeric olefins having from 5 to 24 carbon atoms by two-stage hydroformylation in the presence of a cobalt catalyst or rhodium catalyst at elevated temperature and at elevated pressure, which comprises selectively hydrogenating the first hydroformylation stage reaction mixture, separating the hydrogen mixture in a distillation into crude alcohol and low-boilers predominantly consisting of olefins, passing these low-boilers to the second hydroformylation stage, again selectively hydrogenating the second hydroformylation stage reaction mixture, again separating the hydrogenation mixture in a distillation into crude alcohol and low-boilers, working up the crude alcohol by distillation to pure alcohol and taking off at least some of the low-boilers to discharge saturated hydrocarbons.

In a preferred embodiment of the invention, the expanded reaction mixtures from both hydroformylation stages are separated from the hydroformylation catalyst prior to the selective hydrogenation.

Various other objects, features and attendant advantages of the present invention will be more fully appreciated as the same becomes better understood from the following detailed description when considered in connection with the accompanying drawings.

DESCRIPTION OF THE INVENTION

As described above, the present invention relates to process for preparing higher oxo alcohols from mixtures of isomeric olefins having from 5 to 24 carbon atoms by two-stage hydroformnylation in the presence of a cobalt catalyst or rhodium catalyst at elevated temperature and at elevated pressure, by:

(a) selectively hydrogenating a reaction mixture obtained by hydroformylating isomeric olefins having from 5 to 24 carbon atoms;

(b) distilling the hydrogenation mixture from (a) into crude alcohol and low-boilers, wherein the low-boilers comprise unreacted olefins from the hydroformylation of the isomeric olefins;

(c) hydroformylating the low-boilers from (b);

(d) selectively hydrogenating the hydroformylation reaction mixture from (c);

(e) distilling the hydrogenation mixture from (d) into crude alcohol and low-boilers;

(f) distilling the crude alcohol to obtain a purified alcohol; and (g) taking at least a portion of low-boilers which comprise saturated hydrocarbons.

Figure 1:
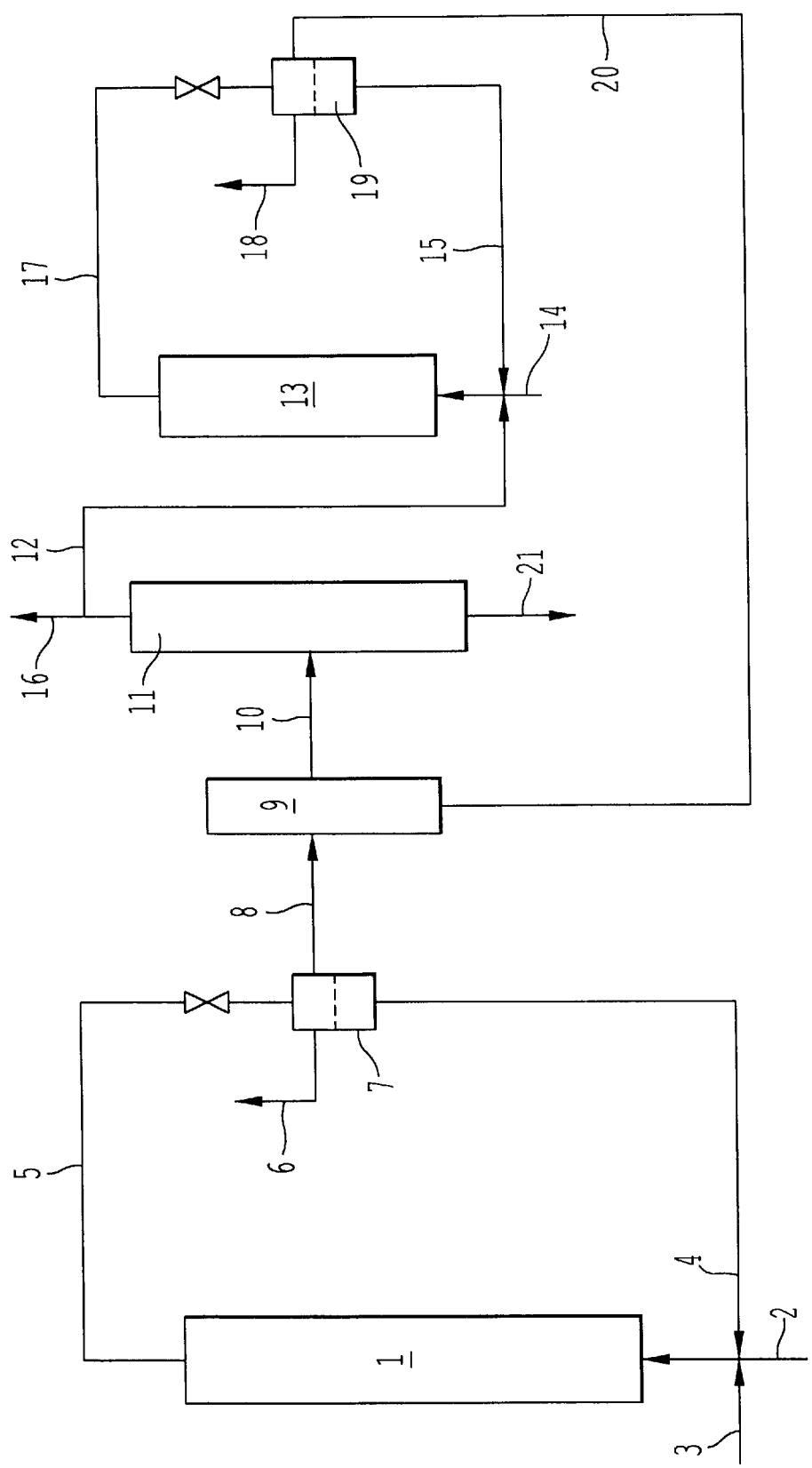
FIG. 1: a block diagram of a plant in which the inventive process may be carried out continuously.

The inventive process may be carried out batchwise or, preferably, continuously. Several process variants are possible for the continuous procedure. In FIG. 1, as an example, the block diagram of a plant is shown in which the process may be carried out continuously. The olefin mixture 2, synthesis gas (carbon monoxide and hydrogen) 3 and catalyst 4 are introduced into the first hydroformylation reactor 1. The hydroformylation mixture 5 is expanded, the expansion gas 6 (unconsumed synthesis gas) is taken off and the expanded hydroformylation mixture 5 is freed from catalyst 4 in the first catalyst removal stage 7, which catalyst, if appropriate after supplementation by fresh catalyst, is recirculated to the first hydroformylation reactor 1. The catalyst-freed hydroformylation mixture 8 is passed into the selective hydrogenation stage 9 in which the aldehydes and by-products present in the mixture, such as acetals of the aldehydes and esters of the alcohols, in particular their formates, are hydrogenated to the alcohols. The low-boilers 12 are removed from the hydrogenation mixture 10 in the distillation 11, which low-boilers predominantly consist of unreacted isomeric olefins and are conducted into the second hydroformylation reactor 13, into which synthesis gas 14 and catalyst 15 are also introduced. Some of the low-boilers 12 are discharged as residual low-boilers 16. The hydroformylation mixture 17 from the second hydroformylation reactor 13 is in turn expanded and expansion gas 18 is taken off. The expanded hydroformylation mixture 17 is freed from catalyst 15 in the second catalyst separation stage 19, which catalyst, again if appropriate after supplementation, is recirculated to the second hydroformylation reactor 13, and, as catalyst-depleted hydrofornylation mixture 20, is transferred to the selective hydrogenation 9. There, it is selectively hydrogenated together with the catalyst-freed hydroformylation mixture 8 from the first hydroformylation reactor 1. The crude alcohol 21 taken off from the distillation 11 is worked up to pure alcohol in a further distillation which is not shown.

Thus, the invention includes, as one embodiment, a process for preparing higher oxo alcohols, by:

(1) selectively hydrogenating a reaction mixture obtained by hydroformylating isomeric olefins having from 5 to 24 carbon atoms;

(2) distilling the hydrogenation mixture from (1) into crude alcohol and low-boilers,
wherein the low-boilers comprise unreacted olefins from the hydroformylation of the isomeric olefins;

(3) hydroformylating the low-boilers from (2);

(4) recirculating the hydroformylation reaction mixture from (3) to (1); and (5) distilling the crude alcohol to obtain a purified alcohol, wherein (1), (2), (3), (4) and (5) are conducted at the same time.

Figure 2:
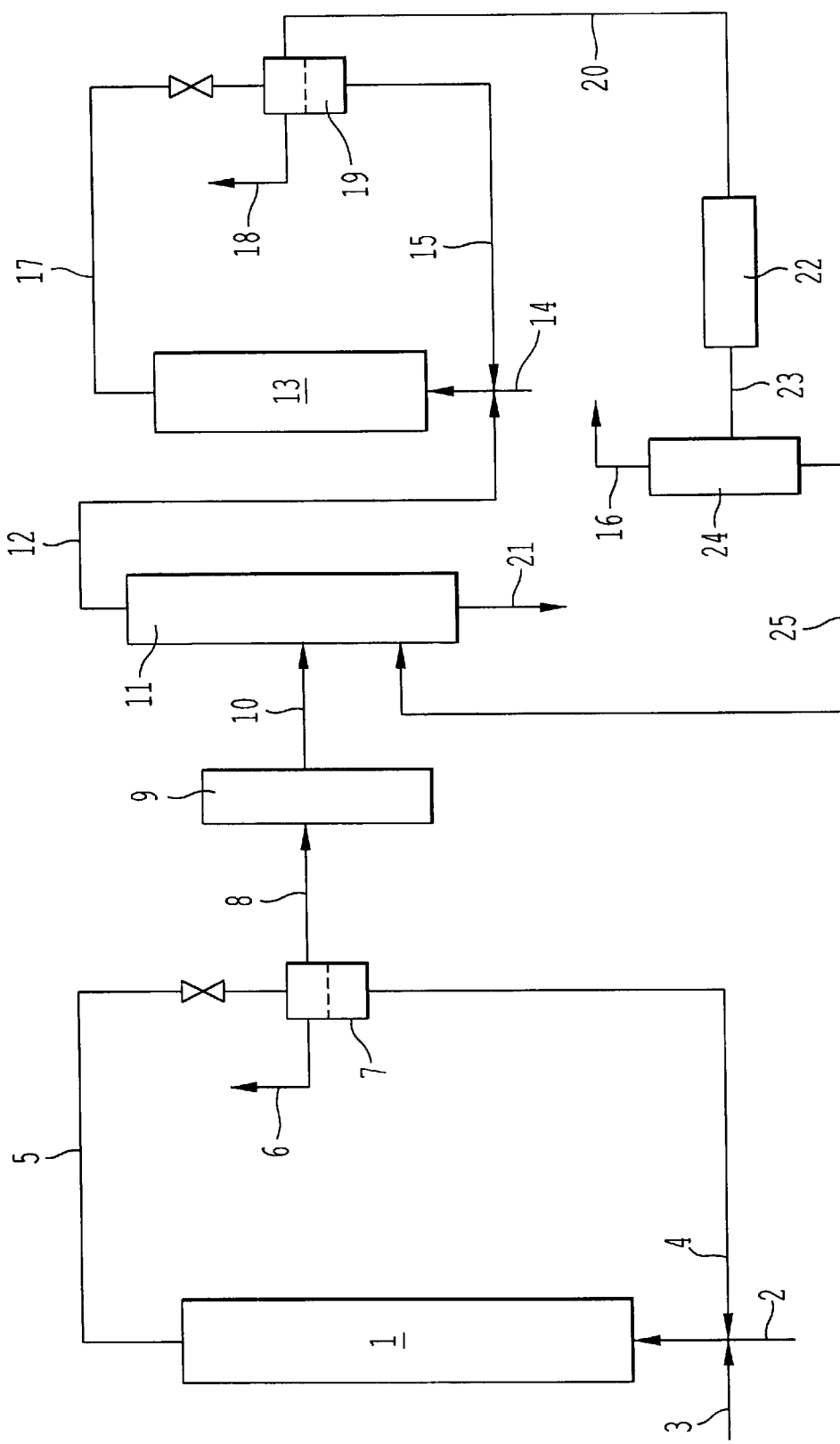
FIG. 2: a block diagram of another plant in which the inventive process may be carried out continuously.

The block diagram of an alternative second continuous process variant for carrying out the process according to the invention is shown in FIG. 2. The olefin mixture 2, synthesis gas 3 and catalyst 4 are introduced into the first hydroformylation reactor 1. The hydroformylation mixture 5 is expanded, the expansion gas 6 is taken off and the expanded hydroformylation mixture is freed from catalyst 4 in the first catalyst removal stage 7, which catalyst, if appropriate after supplementation by fresh catalyst, is recirculated to the first hydroformylation reactor 1. The catalyst-freed hydroformylation mixture 8 is passed into the first selective hydrogenation stage 9, in which the aldehydes and the acetals and esters present as by-products, in particular the formates of the alcohols, are hydrogenated to the alcohols. The low-boilers 12 are separated off from the first hydrogenation mixture 10 in the first distillation stage 11, which low-boilers predominantly consist of unreacted isomeric olefins and are passed to the second hydroformylation reactor 13, into which synthesis gas 14 and catalyst 15 are also introduced. The hydroformylation mixture 17 from the second hydroformylation reactor 13 is in turn expanded, and expansion gas 18 is taken off. The expanded hydroformylation mixture 17 is freed from catalyst 15 in the second catalyst removal stage 19, which catalyst in turn, if appropriate after supplementation by fresh catalyst, is recirculated to the second hydroformylation reactor 13, and as catalyst-depleted hydroformylation mixture 20, is passed into a second comparatively small selective hydrogenation stage 22. The second hydrogenation mixture 23 is fractionated in the second, comparatively small distillation stage 24 into paraffin-rich low-boilers 16, which are taken off, and crude alcohol 25 which is passed to the first distillation stage 11 and is there distilled together with the first hydrogenation mixture 10. The crude alcohol 21 may in turn worked up to pure alcohol in a further distillation which is not shown.

Thus, the invention also includes, as another embodiment, a process for preparing higher oxo alcohols, by:

(1) selectively hydrogenating a reaction mixture obtained by hydroformylating isomeric olefins having from 5 to 24 carbon atoms;

(2) distilling the hydrogenation mixture from (1) into crude alcohol and low-boilers,
wherein the low-boilers comprise unreacted olefins from the hydroformylation of the isomeric olefins;

(3) hydroformylating the low-boilers from (2);

(4) selectively hydrogenating the hydroformylation reaction mixture from (3);

(5) distilling the hydrogenation mixture from (4) into crude alcohol and low-boilers;

(6) combining the crude alcohol from (5) with the crude alcohol from (2); and (7) distilling the crude alcohol from (6) to obtain a purified alcohol,
wherein (1), (2), (3), (4), (5), (6) and (7) are conducted at the same time.

An essential difference between the two process procedures is that according to FIG. 1 only one selective hydrogenation 9 is provided in which the two catalyst-depleted hydroformylation mixtures 8 and 20 are hydrogenated, and only one distillation stage 11 in which the hydrogenation mixture 10 is separated, whereas according to FIG. 2 the second hydroformylation mixture 20 is hydrogenated in a second selective hydrogenation 22 and the hydrogenation mixture is separated in a second distillation stage 24. The variant according to FIG. 2 has higher capital costs because additional, but comparatively small apparatuses are required. In compensation, the olefin is more substantially utilized, since the low-boilers 16 according to FIG. 2 are smaller in quantity than the low-boilers 16 according to FIG. 1 and are in addition substantially free of olefins, whereas the low-boilers 16 according to FIG. 1 still comprise considerable amounts of olefins.

Hydroformylation

The starting materials for the hydroformylation are mixtures of monoolefins having from 5 to 24 carbon atoms and a terminal or middle-position C—C double bond, such as 1- or 2-pentene, 2-methyl-1-butene, 1-, 2- or 3-hexene, the isomeric $C_6$ olefin mixture (dipropene) produced in the dimerization of propene, 1-heptene, 2- or 3-methyl-1-hexene, 1-octene, the isomeric $C_8$ olefin mixture (dibutene) produced in the dimerization of butenes, 1-heptene, 1-nonene 2- or 3-methyl-1-octene, the isomeric $C_9$ olefin mixture (tripropene) produced in the trimerization of 1-propene, 1-, 2- or 3-decene, 2-ethyl-1-octene, 1-dodecene, the isomeric $C_{12}$ olefin mixture (tetrapropene or tributene) produced in the tetramerization of propene or the trimerization of butenes, 1-tetradecene 1- or 2-hexadecene, $C_{16}$ olefin mixtures (tetrabutene) produced in the tetramerization of butenes, and olefin mixtures prepared by cooligomerization of olefins having different carbon numbers (preferably 2 to 4), if appropriate after separating off by distillation into fractions of identical or similar carbon number. Preferred starting materials are $C_8$, $C_9$, $C_{12}$ or $C_{16}$ olefin mixtures.

Well-known conditions for the hydroformylation in the two stages may be used. Rhodium catalysts or preferably in both stages cobalt catalysts are therefore employed, with or without complex-stabilizing additions, such as organic phosphines or phosphites. The temperatures and the pressures can vary within broad ranges, depending on catalyst and olefin mixture. Since the more reactive olefins react preferentially in the first stage, in the second hydroformylation stage, expediently, more energetic reaction conditions with respect to temperature, amount of catalyst etc. are established. For a given olefin mixture, the optimum conditions for the two hydroformylation stages may be established without difficulty by experiment A description of the hydroformylation of olefins is given, for example, in J. Falbe, New Syntheses with Carbon Monoxide, Springer-Verlag Heidelberg-New York, 1980, pages 99 ff., and in Kirk-Othmer, Encyclopedia of Chemical Technology, Volume 17, 4th edition, John Wiley & Sons, pages 902–919 (1996). Both of these publications are incorporated by reference.

Generally, the hydroformylation is carried out in the first stage in such a manner that from 50 to 90%, preferably from 60 to 85%, of the fed olefin mixture is reacted. Obviously, the hydroformylation reactors and the other apparatuses must be designed accordingly.

The degree of conversion of the olefins in the first hydrofonnylation stage is restricted to the desired value by altering the hydroformylation reaction conditions appropriately. By selecting lower reaction temperatures and/or catalyst concentrations and shorter residence times, the olefin conversion rate in the reactor can be decreased. The degree of conversion of the olefins in the first reactor is determined on the basis of the amount and composition of the fresh olefin mixture 2 and of the amount and composition of the hydroformylation mixture 5. The overall degree of conversion is determined on the basis of the amount and composition of the fresh olefin mixture 2 and of the amount and composition of the discharged low-boilers (16 according to the both figures). To determine the olefin contents in the various mass streams, gas-chromatograpic analysis may be used.

Catalyst Removal

The hydroformylation reaction mixtures are, as described above, preferably first freed from catalyst. If a cobalt catalyst was used, this can be achieved by pressure reduction, separating off the aqueous catalyst phase, oxidizing with air or oxygen the cobalt carbonyl compounds remaining in the hydroformylation mixture and extracting the resulting cobalt compounds with water or aqueous acid. Decobalting processes are well known, see, for example, J Falbe, loc. cit., 164, 165 (BASF Process), Kirk-Othmer. loc. cit. and EP-0 850 905 A1 incoporated herein by reference. If a rhodium compound served as hydroformylation catalyst, it can be removed from the hydrofonnylation mixture as distillation residue by means of thin-film evaporation.

If the preferred cobalt catalysts were used, the first hydroformylation stage reaction mixtures freed from catalyst comprise, depending on the degree of conversion, generally 8–45% by weight, usually 15–35% by weight of low-boilers having a lower boiling point than the aldehydes, principally olefins, in addition the corresponding saturated hydrocarbons and water and methanol, in addition 30–80% by weight of aldehydes, 5–30% by weight of alcohols, up to 10% by weight of formates of the alcohols and 0.5–5% by weight of high-boilers having a higher boiling point than the alcohols.

In the second hydroformylation stage reaction mixtures, generally 10–40% by weight, usually 15–30% by weight, of low-boilers, including less olefins and many saturated hydrocarbons and water and methanol, in addition 30–70% by weight of aldehydes, 5–40% by weight of alcohols, up to 10% by weight of formnates of these alcohols and 3–12% by weight of high-boilers having a higher boiling point than the alcohols are then present.

If rhodium catalysts were used, the reaction mixtures comprise considerably less paraffins and formates.

Selective Hydrogenation

The selective hydrogenation of the reaction mixtures from both hydroformylation stages, preferably freed from catalyst, is a feature of the inventive process. As a result, the aldehydes and certain accompanying substances, including acetals of the aldehydes and esters of the alcohols and of these, in particular, the formates, are hydrogenated to the desired alcohols. In the course of this, the unreacted olefins are not hydrogenated or are virtually not hydrogenated, so that high yields based on the olefin mixtures used are achieved. Less than 5% of the olefins used are lost due to hydrogenation to the saturated hydrocarbons.

Selective hydrogenation of hydroformylation mixtures is the subject matter of the German patent application 198 42 370.5, incorporated herein by reference. The hydroformylation reaction mixtures are hydrogenated with hydrogen at elevated temperature and at elevated pressure on a supported catalyst which comprises, as active components, copper, nickel and chromium.

Preferred catalysts of this type are supported catalysts which comprise, as active components, copper and nickel at concentrations in each case of from 0.3 to 15% by weight, chromium at a concentration of from 0.05 to 3.5% by weight and an alkali metal component at a concentration of from 0.01 to 1.6% by weight, preferably 0.02–1.2% by weight, in each case based on the supported catalyst. Another advantageous supported catalyst comprises copper, nickel and chromium in the specified amounts, but no alkali metal component. Suitable support substances are, in particular, silicon dioxide and aluminum oxide. The amounts specified are based on the catalyst which is prepared as described below and has not yet been reduced.

In the hydrogenation, the aldehydes in the reaction mixtures of both hydroformylation stages are in each case hydrogenated to the corresponding alcohols in only one hydrogenation stage step with conversion rates greater than 98% at a selectivity of greater than 99%. The esters and acetals are likewise converted into the desired alcohols. The starting olefins present in the mixture remain surprisingly by far for the most part unchanged, although the preferred supported catalysts, under comparable conditions, also hydrogenate virtually quantitatively the olefinic double bond in 2-ethylhex-2-enal (EP 0 326 674 A2). The hydrogenation can be carried out in the low-pressure region of below 30 bar and at high space-time yields.

The catalyst components can be distributed homogeneously in the pores of a support material or enriched in its edge zones. In the former case, an aqueous solution is made up which comprises the components in the form of metal salts and whose volume expediently roughly corresponds to 0.8 times the pore volume of the support material. As copper salts, nickel salts and chromium salts as catalyst precursor, use is advantageously made of those which are converted on heating into oxides, such as nitrates and acetates. If the catalyst is to contain an alkali metal component, this can be introduced together with chromium in the form of alkali metal chromate or alkali metal dichromate, in particular as sodium chromate or sodium dichromate. The metal salt concentration in the solution depends on the desired concentration of the respective component in the finished catalyst. The metal salt solution is then sprayed onto the non-preheated support material, situated in a coating drum, and penetrates into the pores thereof. The catalyst is then dried.

If it is desired to have a catalyst with components which are enriched in the edge zones of a porous or a more or less pore-free support material, the metal salt solution can be sprayed onto the preheated support material and the support material can be further heated during the spraying, so that the water evaporates and the catalyst components are fixed essentially on the surface of the support material.

After the catalyst components are applied, the catalysts of both said types are calcined, i.e. depending on the catalyst precursor used, heated to temperatures of 200–400° C., as a result of which the catalyst precursors are converted into the oxalic state. The catalyst is then reduced with hydrogen at said hydrogenation temperatures. The reduction can be performed just after the catalyst is prepared or expediently not until in the hydrogenation reactor.

The catalysts are preferably used in a form in which they offer a low resistance to flow, e.g. in the form of granules, pellets or shaped bodies such as tablets, cylinders or rings. They are expediently activated prior to use by heating in a hydrogen stream, e.g. at the hydrogenation temperatures described above, if they have not been reduced in the reactor.

The hydrogenation can be carried out continuously or batchwise and either in the gas phase or in the liquid phase. Hydrogenation in the liquid phase is preferred, since the gas-phase process requires a higher energy consumption, because of the necessary circulation of large gas volumes. In addition there is the fact that evaporating aldehydes having an increasing carbon number requires more and more energy, and, in addition, the starting material loading in the reduction gas decreases, so that a gas-phase process in the case of aldehydes having a carbon number greater than about 8 makes it scarcely possible still to carry out the overall process economically.

Various process variants can be selected for the liquid-phase hydrogenation. It can be carried out adiabatically or virtually isothermally, i.e. having a temperature rise of <10° C., in a single stage or two stages. In the latter case, both reactors, preferably tube reactors, can be operated adiabatically or virtually isothermally or one can be operated adiabatically and the other virtually isothermally. In addition, it is possible to hydrogenate the hydroformylation mixtures in a straight pass or with product recycling. The reactors can be operated as concurrent flow reactors with a trickle bed (trickle flow) or preferably with high liquid flow rates (pulse flow). In the interest of a high space-time yield, the reactors are preferably operated with high liquid flow rates of 5–100 $m^3$, in particular 15–50 $m^3$ per $m^2$ of cross section of the empty reactor and hour. If a reactor is operated isothermally and in a straight pass, the liquid hourly space velocity (LHSV) values can be between 0.1 and 10 $h^{-1}$, preferably between 0.5 and 5 $h^{-1}$.

The liquid-phase hydrogenation is generally carried out at an overall pressure of from 5 to 30 bar, in particular between 15 and 25 bar. The gas-phase hydrogenation can also be carried out at lower pressures, with correspondingly greater gas volumes. The reaction temperatures, in the case of hydrogenations in the liquid or gas phase, are generally between 120 and 220° C., in particular between 140 and 180° C.

Separation of the Hydrogenation Mixtures by Distillation

After the hydrogenation, the reaction mixtures are worked up by distillation in manner known per se. Low-boilers are removed as overhead product, which low-boilers predominantly comprise olefins and in addition saturated hydrocarbons. According to FIG. 1, the low-boilers from both hydroformylation stages are starting material for the second hydroformylation stage. In this process variant, however, some of these low-boilers are discharged, so that the concentration of the inert saturated hydrocarbons produced by hydrogenation of the olefins in the hydroformylation stages is kept to an acceptable level of at most 60%. In the process variant according to FIG. 2, all of the low-boilers from the first distillation stage are passed to the second hydroformylation stage, and the saturated hydrocarbons are discharged as a comparatively small low-boiler fraction of the second distillation.

The hydrogenation mixtures are generally distilled at reduced pressure, e.g. at an absolute pressure of 400–900 mbar. The crude alcohol which is produced as bottom product in the distillation can be worked up to pure alcohol in a conventional manner by distillation.

Having generally described this invention, a further understanding can be obtained by reference to certain specific examples which are provided herein for purposes of illustration only and are not intended to be limiting unless otherwise specified.

EXAMPLES

Example 1 (Comparative example)

Nonanols by Single-stage Hydroformylation of di-n-butene

In a 5 l high-pressure autoclave which was equipped with an agitator and electrical heating, 2000 g of di-n-butene (composition in Table 1, column 2) were hydroformylated in the presence of a cobalt catalyst at 185° C. and a synthesis gas pressure kept constant at 280 bar. The synthesis gas comprised 50% by volume of CO and 50% by volume of $H_2$.

To prepare the cobalt hydridocarbonyls. e.g. $HCo(CO)_4$, serving as catalyst, as catalyst precursor, use was made of an aqueous cobalt acetate solution containing 1% by weight of Co. The cobalt acetate solution was treated with synthesis gas, with stirring for 7 h at 170° C. and 280 bar. After cooling to room temperature and expansion, the cobalt carbonyls formed were transferred to the organic phase by extraction with di-n-butene. After removing the aqueous phase, the di-n-butene loaded with cobalt carbonyls having a content of 0.021% by weight of Co (calculated as metal) was hydroformylated under the abovementioned reaction conditions for 3 hours.

After cooling to room temperature, the reaction mixture was emptied, depressurized, from the autoclave and freed from cobalt catalyst by treatment with 5% strength acetic acid and air at 80° C. 2487 g of decobalted hydroformylation mixture were obtained, which were analyzed by gas chromatography. The results are listed in Table 2, column 2. According to these, a di-n-butene conversion rate of 92.3% was achieved at a selectivity of product of value of 87.9%, equivalent to a yield of product of value of 81.1%, based on di-n-butene used. Products of value were considered to be $C_9$ aldehydes, $C_9$ alcohols and (iso)nonyl formates.

Example 2
Nonanols by Two-stage Hydroformylation—1st Stage

In a 5 l high-pressure autoclave which was equipped with an agitator and electrical heating, 2000 g of di-n-butene (composition in Table 1, column 2) were hydroformylated in the presence of a cobalt catalyst at 170° C. and a synthesis gas pressure kept constant at 280 bar. The synthesis gas again comprised 50% by volume of CO and 50% by volume of $H_2$.

The cobalt catalyst was prepared as in Example 1 and transferred to the di-n-butene. The concentration of the catalyst was 0.019% by weight of Co based on the di-n-butene. The di-n-butene loaded with cobalt carbonyls was hydroformylated under the abovementioned reaction conditions for 2 hours. The hydroformylation mixture was freed from cobalt catalyst as in Example 1.

This hydroformylation solution was repeated three times under the same conditions. The hydroformylation mixtures were combined after removal of the cobalt catalyst. This produced 9412 g of reaction mixture which had the composition specified in Table 2, column 3, according to GC analysis. A di-n-butene conversion rate of 67.6% was then achieved at a selectivity for product of value of 94.5%, equivalent to a yield of product of value of 63.9%, based on di-n-butene used. Products of value were again considered to be $C_9$ aldehydes, $C_9$ alcohols and (iso)nonyl formates.

Example 3
Nonanols by Two-stage Hydroformylation—2nd Stage 7500 g of the reaction mixture from Example 2 were selectively hydrogenated with retention of the olefins to give the product of value $C_9$ alcohol. The hydrogenation was carried out batchwise in the liquid phase in a 20 l autoclave at 175° C. and 20 bar $H_2$ pressure in the presence of a supported catalyst containing 12.1% by weight of Cu, 3.0% by weight of Ni and 2.5% by weight of Cr on aluminum oxide as support material. The unreacted olefins were then distilled off as low-boilers from the products of value and the high-boilers from the hydrogenation mixture.

The low-boiler fraction, according to GC analysis, comprised, in addition to 98.5% by weight of hydrocarbons of which 87.9% by weight were $C_8$ olefins around 1.5% by weight of methanol which had been formed by hydrogenation of (iso)nonyl formates. The distribution of isomers in the $C_8$ isomer mixture is listed in Table 1, column 3. In comparison with the fresh di-n-butene containing 23% by weight of dimethylhexenes, this $C_8$ isomeric mixture containing 44% by weight of dimethylhexenes comprised considerably greater amounts of these less reactive $C_8$ isomers.

2000 g of this $C_8$ olefin isomer mixture enriched with dimethylhexenes and comprising 10.6% by weight of $C_8$ paraffins were hydroformylated in a 5 l autoclave in the presence of a cobalt catalyst in the manner described in Example 1 at 185° C. and a synthesis gas pressure of 280 bar. Again a synthesis gas containing 50% by volume of CO and 50% by volume of $H_2$ was used. At a cobalt content of 0.031% by weight, based on the $C_8$ olefin mixture, this mixture was hydroformylated for 3 hours at a synthesis gas pressure which was kept constant.

The hydroformylation mixture was expanded and freed from cobalt catalyst as described in Example 1. This produced 2438 g of a decobalted hydroformylation mixture whose composition according to GC analysis is given in Table 2, column 4. According to this, a $C_8$ olefin conversion rate of 91.3% was achieved at a selectivity for product of value of 83.0%, equivalent to a yield of product of value of 75.8%, based on di-n-butene used. Products of value were considered to be $C_9$ aldehydes. $C_9$ alcohols and (iso)nonyl formates.

If Example 2, as first hydroformylation stage, and Example 3, as second hydroformylation stage, of the process according to the invention are combined, after both stages, an overall olefin conversion rate of 97.1% was achieved, at a selectivity for product of value of 91.5%, equivalent to a total yield of product of value of 88.8%, based on olefin mixture used.

In comparison with the single-stage hydroformylation according to Example 1, there is therefore an increase in the yield of product of value by around 8 percentage points.

TABLE 1

Distribution of the $C_8$ isomers in the feed olefin mixture

| 1<br>$C_8$ isomers | 2<br>di-n-butene starting material Examples 1 and 2<br>(% by weight) | 3<br>$C_8$ olefin mixture starting material Example 3<br>(% by weight) |
| --- | --- | --- |
| Dimethylhexenes | 23 | 44 |
| 3-Methylheptenes | 62 | 51 |
| n-Octenes | 15 | 5 |

TABLE 2

Composition of hydroformylation mixtures

| 1<br>Composition according to GC analysis | 2<br>Example 1<br>(% by weight) | 3<br>Example 2<br>(% by weight) | 4<br>Example 3<br>(% by weight) |
| --- | --- | --- | --- |
| $C_8$ olefins | 6.2 | 27.4 | 7.0 |
| $C_8$ paraffins | 3.3 | 2.4 | 4.5 |
| Isononanals | 55.1 | 48.7 | 51.2 |
| Esters/isononyl formates | 4.5 | 2.0 | 8.8 |
| Isononanols | 23.9 | 18.5 | 18.8 |
| Residue | 7.0 | 1.0 | 9.8 |

Obviously, numerous modifications and variations of the present invention are possible in light of the above teachings. It is therefore to be understood that within the scope of the appended claims, the invention may be practiced otherwise than as specifically described herein.

This application is based on German Patent Application No. 198 42 368.3, filed on Sep. 16, 1998, and incoporated herein by reference.

What is claimed is:

1. A process for preparing higher oxo alcohols from mixtures of isomeric olefins having from 5 to 24 carbon atoms by two-stage hydroformylation in the presence of a cobalt catalyst or rhodium catalyst at elevated temperature and at elevated pressure, comprising:

(a) selectively hydrogenating a reaction mixture obtained by hydroformylating isomeric olefins having from 5 to 24 carbon atoms;

(b) distilling the hydrogenation mixture from (a) into crude alcohol and low-boilers, wherein the low-boilers comprise unreacted olefins from the hydroformylation of the isomeric olefins;
(c) hydroformylating the low-boilers from (b);
(d) selectively hydrogenating the hydroformylation reaction mixture from (c);
(e) distilling the hydrogenation mixture from (d) into crude alcohol and low-boilers;
(f) distilling the crude alcohol to obtain a purified alcohol; and
(g) discharging at least a portion of low-boilers which comprise saturated hydrocarbons.

2. The process of claim 1, wherein the reaction mixtures from both hydroformylations are expanded and separated from the hydroformylation catalyst prior to the selective hydrogenation.

3. The process of claim 1, wherein $C_8$, $C_9$, $C_{12}$ or $C_{16}$ olefin mixtures are used as starting materials for the hydroformylation.

4. The process of claim 1, wherein cobalt catalysts are employed in both hydroformylation stages.

5. The process of claim 1, wherein only one selective hydrogenation is provided in which the reaction mixtures from both hydroformylation stages are selectively hydrogenated in a single reaction and only one distillation in which the hydrogenation reaction mixture is separated is provided.

6. The process of claim 5, wherein some of the low-boilers from the distillation are taken off in order to discharge paraffins.

7. The process of claim 1, wherein (a) and (d) are conducted as two separate reactions and (b) and (e) are conducted as two separate distillations.

8. The process of claim 7, wherein the low-boilers from (e) are taken off in order to discharge paraffins.

9. The process of claim 1, wherein the hydroformylation reaction mixtures are selectively hydrogenated at elevated temperature and at elevated pressure on a supported catalyst which comprises, as active components, copper, nickel and chromium.

10. The process of claim 9, wherein the supported catalyst comprises, as active components, copper and nickel at concentrations in each case of from 0.3 to 15% by weight, chromium at a concentration of from 0.05 to 3.5% by weight and an alkali metal component at a concentration of from 0.01 to 1.6% by weight, in each case based on the supported catalyst.

11. The process of claim 10, wherein the concentration of the alkali metal component is from 0.2 to 1.2% by weight.

12. The process of claim 10, wherein the supported catalyst does not contain an alkali metal component.

13. The process of claim 9, wherein the catalyst support material is silicon dioxide or aluminum oxide.

14. The process of claim 1, wherein the hydrogenation is carried out continuously or batchwise in a liquid phase.

15. The process of claim 1, wherein the hydrogenation is carried out in the liquid phase under an overall pressure of from 5 to 30 bar.

16. The process of claim 15, wherein the overall pressure is from 15 to 25 bar.

17. The process of claim 1, wherein the hydrogenation is carried out at from 120 to 220° C.

18. The process of claim 17, wherein the hydrogenation is carried out at from 140 to 180° C.

19. The process of claim 1, wherein the hydrogenation is carried out in the liquid phase and with liquid flow rates of 5–100 $m^3$ per $m^2$ of cross section of the empty reactor and hour.

20. The process of claim 19, wherein the liquid flow rate is 15–50 $m^3$ per $m^2$ of cross section of the empty reactor and hour.

21. A process for preparing higher oxo alcohols, comprising:
(1) selectively hydrogenating a reaction mixture obtained by hydroformylating isomeric olefins having from 5 to 24 carbon atoms;
(2) distilling the hydrogenation mixture from (1) into crude alcohol and low-boilers,
wherein the low-boilers comprise unreacted olefins from the hydroformylation of the isomeric olefins;
(3) hydroformylating the low-boilers from (2);
(4) recirculating the hydroformylation reaction mixture from (3) to (1); and
(5) distilling the crude alcohol to obtain a purified alcohol,
wherein (1), (2), (3), (4) and (5) are conducted at the same time.

22. A process for preparing higher oxo alcohols, comprising:
(1) selectively hydrogenating a reaction mixture obtained by hydroformylating isomeric olefins having from 5 to 24 carbon atoms;
(2) distilling the hydrogenation mixture from (1) into crude alcohol and low-boilers,
wherein the low-boilers comprise unreacted olefins from the hydroformylation of the isomeric olefins;
(3) hydroformylating the low-boilers from (2);
(4) selectively hydrogenating the hydroformylation reaction mixture from (3);
(5) distilling the hydrogenation mixture from (4) into crude alcohol and low-boilers;
(6) combining the crude alcohol from (5) with the crude alcohol from (2); and
(7) distilling the crude alcohol from (6) to obtain a purified alcohol,
wherein (1), (2), (3), (4), (5), (6) and (7) are conducted at the same time.

* * * * *

UNITED STATES PATENT AND TRADEMARK OFFICE
CERTIFICATE OF CORRECTION

PATENT NO. : 6,331,657 B1
DATED : December 18, 2001
INVENTOR(S) : Kaizik et al.

It is certified that error appears in the above-identified patent and that said Letters Patent is hereby corrected as shown below:

<u>Title page,</u>
Item [45], the Date of Patent should read:
-- [45] Date of Patent: *Dec. 18, 2001 --

Item [75], the Inventors' information should read:

-- [75] Inventors: Alfred Kaizik, Marl; Dirk Roettger, Recklinghausen; Bernhard Scholz, Marl; Klaus-Dieter Wiese, Haltern; Walter Toetsch, Marl; Wilfried Bueschken, Haltern; Franz Nierlich, Marl, all of (DE) --

The Notice information should read:

-- [*] Notice: This patent on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days. --

UNITED STATES PATENT AND TRADEMARK OFFICE
CERTIFICATE OF CORRECTION

PATENT NO.    : 6,331,657 B1
DATED         : December 18, 2001
INVENTOR(S)   : Kaizik et al.

It is certified that error appears in the above-identified patent and that said Letters Patent is hereby corrected as shown below:

<u>Title page, cont'd,</u>
Item [30], the Foreign Application Priority information should read:

-- [30]  Foreign Application Priority Data

Sep. 16, 1998   (DE)......................... 198 42 368 --

Signed and Sealed this

Sixth Day of August, 2002

*Attest:*

JAMES E. ROGAN
*Attesting Officer*         *Director of the United States Patent and Trademark Office*

UNITED STATES PATENT AND TRADEMARK OFFICE
CERTIFICATE OF CORRECTION

PATENT NO. : 6,331,657 B1
DATED : December 18, 2001
INVENTOR(S) : Kaizik et al.

It is certified that error appears in the above-identified patent and that said Letters Patent is hereby corrected as shown below:

<u>Title page,</u>
Item [45], the Date of Patent should read:
-- [45] Date of Patent: *Dec. 18, 2001 --

Item [75], the Inventors' information should read:

-- [75] Inventors: Alfred Kaizik, Marl; Dirk Roettger, Recklinghausen; Bernhard Scholz, Marl; Klaus-Dieter Wiese, Haltern; Walter Toetsch, Marl; Wilfried Bueschken, Haltern; Franz Nierlich, Marl, all of (DE) --

The Notice information should read:

-- [*] Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days. --

UNITED STATES PATENT AND TRADEMARK OFFICE
CERTIFICATE OF CORRECTION

PATENT NO.    : 6,331,657 B1
DATED         : December 18, 2001
INVENTOR(S)   : Kaizik et al.

It is certified that error appears in the above-identified patent and that said Letters Patent is hereby corrected as shown below:

<u>Title page, cont'd,</u>
Item [30], the Foreign Application Priority information should read:

-- [30]   Foreign Application Priority Data

Sep. 16, 1998   (DE)......................... 198 42 368 --

This certificate supersedes Certificate of Correction issued August 6, 2002.

Signed and Sealed this

Twenty-fourth Day of December, 2002

JAMES E. ROGAN
*Director of the United States Patent and Trademark Office*